(12) United States Patent
Radl et al.

(10) Patent No.: US 10,959,700 B2
(45) Date of Patent: Mar. 30, 2021

(54) NEEDLE GUIDE FOR ULTRASOUND PROBE

(71) Applicant: Boehringer Technologies, LP, Phoenixville, PA (US)

(72) Inventors: Christopher L. Radl, Malvern, PA (US); Manuel Seas, McAllen, TX (US)

(73) Assignee: Boehringer Technologies, LP, Phoenixville, PA (US)

( * ) Notice: Subject to any disclaimer, the term of this patent is extended or adjusted under 35 U.S.C. 154(b) by 483 days.

(21) Appl. No.: 16/032,635

(22) Filed: Jul. 11, 2018

(65) Prior Publication Data

US 2019/0059854 A1     Feb. 28, 2019

Related U.S. Application Data

(60) Provisional application No. 62/548,513, filed on Aug. 22, 2017.

(51) Int. Cl.
| | | |
|---|---|---|
| *A61B 17/34* | (2006.01) | |
| *A61B 8/00* | (2006.01) | |
| *A61B 8/08* | (2006.01) | |

(52) U.S. Cl.
CPC .......... *A61B 8/4455* (2013.01); *A61B 8/0841* (2013.01); *A61B 17/3403* (2013.01); *A61B 2017/3411* (2013.01); *A61B 2017/3413* (2013.01)

(58) Field of Classification Search
CPC ...... A61B 2017/3413; A61B 2017/347; A61B 2017/3405; A61B 2017/3411; A61B 17/3403; A61B 8/0833; A61B 8/0841; A61M 5/3287; A61M 25/02
See application file for complete search history.

(56) References Cited

U.S. PATENT DOCUMENTS

| | | | |
|---|---|---|---|
| 4,469,106 A | 9/1984 | Harui | |
| 4,576,175 A | 3/1986 | Epstein | |
| 5,235,987 A | 8/1993 | Wolfe | |
| 5,758,650 A | 6/1998 | Miller et al. | |
| 5,941,889 A * | 8/1999 | Cermak | A61B 8/0833 606/130 |
| 6,203,499 B1 * | 3/2001 | Imling | A61B 8/0833 600/461 |
| 6,296,614 B1 | 10/2001 | Pruter | |
| 6,379,307 B1 | 4/2002 | Filly et al. | |
| 6,814,704 B2 * | 11/2004 | Weilandt | A61B 17/3403 600/461 |
| 7,087,024 B1 | 8/2006 | Pruter | |
| 7,241,267 B2 | 7/2007 | Furia | |
| 7,588,541 B2 | 9/2009 | Floyd et al. | |
| 8,137,281 B2 | 3/2012 | Huang et al. | |
| 10,639,008 B2 * | 5/2020 | Lindekugel | A61B 8/42 |
| 2007/0282205 A1 | 12/2007 | Furia | |

* cited by examiner

*Primary Examiner* — Carolyn A Pehlke
(74) *Attorney, Agent, or Firm* — Caesar Rivise, PC

(57) ABSTRACT

A needle guide for an ultrasonic probe is disclosed. The needle guide includes a pair of pivotable jaws mounted at the end of a pair of elongated arms. The jaws establish a tapering gap between them for receipt of the working head of the ultrasound probe. The needle guide also includes a needle holding section having plural angled slots or channels, each of which is configured for receipt of a needle therein to guide the needle along a respective desired path to a position below the working head of the ultrasound probe so that it can be imaged thereat. The needle guide can be operated by one hand.

15 Claims, 2 Drawing Sheets

NEEDLE GUIDE FOR ULTRASOUND PROBE

CROSS-REFERENCE TO RELATED APPLICATIONS

This utility application claims the benefit under 35 U.S.C. § 119(e) of Provisional Application Ser. No. 62/548,513 filed on Aug. 22, 2017 entitled Needle Guide for Ultrasound Probe. The entire disclosure of this provisional application is incorporated by reference herein.

FIELD OF THE INVENTION

This invention relates generally to needle guides for medical imaging instruments and more particularly to needle guides for mounting onto an ultrasound probe.

BACKGROUND OF THE INVENTION

Ultrasound probes are commonly used for imaging interior portions of a patient's body for various diagnostic reasons. One common use is to enable one to conduct a needle biopsy by mounting a biopsy needle on the probe so that the needle can be extended along a desired trajectory to a desired location within the angle of view of the probe. Another common use is to provide vascular access, e.g., introduce a vascular access needle along a desired path into a femoral artery or other blood vessel to enable it to be viewed by the probe for various intravascular procedures. To that end, various needle guides have been disclosed in the patent literature and are commercially available for mounting on an imaging instrument, e.g., an ultrasound probe, for introducing a needle or other elongated instrument into the body of a patient so that it can be viewed by the imaging instrument. Examples of such devices are found in U.S. Pat. No. 4,469,106 (Harui); U.S. Pat. No. 4,576,175 (Epstein); U.S. Pat. No. 5,235,987 (Wolfe); U.S. Pat. No. 5,758,650 (Miller et al.); U.S. Pat. No. 6,296,614 (Pruter); U.S. Pat. No. 6,379,307 (Filly et al.); U.S. Pat. No. 7,087,024 (Pruter); U.S. Pat. No. 7,241,267 (Furia); U.S. Pat. No. 7,588,541 (Floyd et al.); and U.S. Pat. No. 8,137,281 (Huang et al.); and US 2007/0282205 (Furia).

While the aforementioned needle guides appear suitable for their intended purposes, they nevertheless leave something to be desired from one or more of the standpoints of complexity of construction, cost, ease of use, etc.

Hence, there is a need in the prior art for a needle guide device which overcomes those disadvantages of the prior art. The subject invention addresses that need by providing a needle guide that is very simple in construction, low in cost, effective and easy to use, e.g., it enables a user, e.g., a surgeon to use the ultrasound probe with the needle guide thereon with one hand, leaving the other hand free to insert the needle into the needle guide and from there into the patient.

BRIEF SUMMARY OF THE INVENTION

In accordance with one aspect of this invention there is provided a needle guide configured for releasable mounting on an imaging transducer. The imaging transducer has a longitudinal central axis and working head for providing an image within a field of view of the working head. The needle guide comprises a pair of elongated arms, a pair of jaws, a pair of handles, a bridge section, and a needle holding section. Each of the arms has a distal end portion and a proximal end portion. One of the pair of jaws is mounted on the distal end portion of one of the pair of elongated arms. The other of the pair of jaws is mounted on the distal end portion of the other of the pair of elongated arms. Each of the jaws has an interior facing surface. The interior facing surfaces of the jaws are spaced apart from each other to form a gap therebetween. The gap has a central axis. Each of the interior facing surfaces has a top portion and a bottom portion, with the spacing between the top portions of the interior facing surfaces as measured from the central axis being greater than the spacing between the bottom portions of the interior facing surfaces as measured from the central axis. The pair of handles is configured to be squeezed towards each other. One of the pair of handles is connected to the proximal end portion of one of the pair of elongated arms. The other of the pair of handles is connected to the proximal end portion of the other of the pair of elongated arms. The bridge section is connected between the pair of handles. The bridge section is resilient and configured to bend in response to the squeezing of the pair of handles towards each other to cause the distal end portions of the pair of elongated arms to pivot outward and away from each other to thereby increase the size of the gap to enable the working head of the imaging transducer to be inserted into the gap. The bridge section is configured to automatically cause the distal end portions of the pair of elongated arms to pivot inward and towards each other upon release of the handles to cause the pair of jaws to tightly sandwich the working head of the imaging transducer between the interior facing surfaces thereof. The needle holding section is secured to the bridge section and located between the pair of elongated arms. The needle holding section includes at least one slot or channel therein extending at an angle to the central axis for releasably receiving a needle therein to guide the needle along a path into the field of view of the imaging transducer.

In accordance with one preferred aspect of this invention the needle holding section comprises plural slots or channels. Each of the slots or channels is spaced from the central axis by a distance, with each of the distances being different, and wherein each of the slots or channels is configured for receiving a needle therein to guide the needle along a respective and different path into the field of view of the imaging transducer.

In accordance with another preferred aspect of this invention the plural slots or channel is oriented at a predetermined angle, e.g., 45 degrees, to the central axis.

In accordance with another preferred aspect of this invention the needle holding section comprises indicia located adjacent respective ones of the plural slots or channels.

In accordance with another preferred aspect of this invention each of the interior facing surfaces of the jaws is generally V-shaped.

In accordance with another preferred aspect of this invention the handles are arcuate.

In accordance with another preferred aspect of this invention the bridge section is arcuate.

In accordance with another preferred aspect of this invention the needle guide is an integrally molded unit.

In accordance with another preferred aspect of this invention the at least one slot or channel is configured to accept a 16-18 gauge needle.

DETAILED DESCRIPTION OF THE PREFERRED EMBODIMENTS OF THE INVENTION

Figures 1, 2:
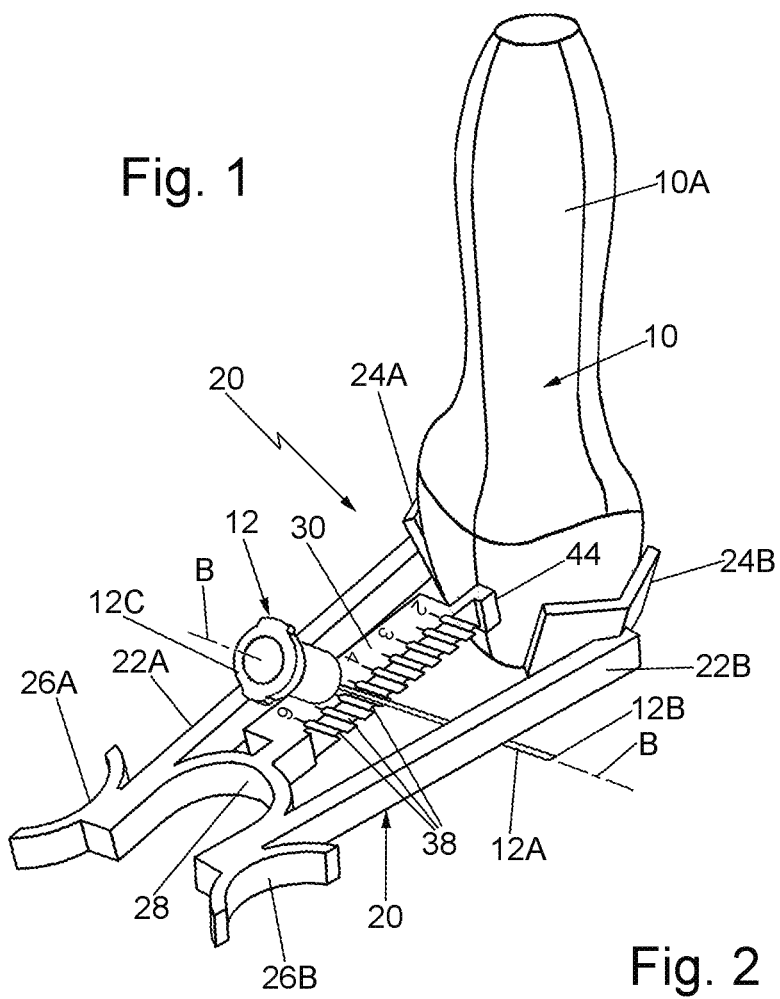
FIG. 1 is an isometric view of an exemplary ultrasonic probe, on which a needle guide constructed in accordance with this invention is shown releasably mounted with the needle guide holding a vascular access needle for introduction into the body of a patient.
FIG. 2 is an exploded isometric view of the ultrasonic probe, the needle guide, and the vascular access needle shown in FIG. 1.

Referring now to the various figures of the drawing wherein like reference characters refer to like parts, there is shown in FIG. 1 one exemplary needle guide device 20 constructed in accordance with this invention. The needle guide 20 is arranged to be releasably mounted on an imaging instrument, e.g., a ultrasound transducer or probe 10 to guide a needle 12, e.g., a vascular access needle, or other thin elongated instrument through a desired path into a vessel, e.g., the femoral artery, while the needle's position is observed on a monitor to which the ultrasound probe is connected. Once the needle is so located the needle guide can be readily removed, leaving the needle in place so that it can be used to accomplish any type of intravascular procedure. It should be pointed out at this juncture that while the needle guide 20 is particularly suited for such use it can be used with other types of elongated instrument on any type of imaging instrument. Thus, the term "needle" as used herein means any type of elongated thin instrument that is arranged to be mounted on some imaging instrument, e.g., an ultrasound probe, and guided to a position inside the body of a patient while being imaged, and once in position being used for performing some type of procedure therein.

Before describing the details of the needle guide 20, a brief description of the ultrasonic probe 10 and a brief description of the intravascular access needle 12 is in order. The probe 10 can be of any conventional construction, and in the embodiment shown includes a proximal portion 10A which serves as a handle for a user to hold the probe. The probe has a longitudinal central axis A. The distal portion of the probe is in the form of a working head 10B at which the transducer's lens is located so that the field of view of the probe is along the axis A.

The vascular access needle 12 is also of conventional construction and includes a hollow linear section or shaft 12A that includes a central passageway extending fully therethrough and centered about a central longitudinal axis B. The distal end of the linear section is in the form of sharp tip 12B. The proximal end of the linear section 12A is in the form of a hollow connector or coupling 12C.

The needle guide 20 is preferably a unitary member formed of any suitable material, such as a plastic, metal, etc., and can be integrally formed, e.g., molded, etc., or assembled from different components which are fixedly secured together to form the unitary member. One particularly suitable material for the needle guide is polycarbonate. While it is preferred that the needle guide be a disposable device, it may be constructed so that it can be reused, e.g., be autoclavable. In any case, the needle guide 20 basically comprises a pair of pivotable arms 22A and 22B, a pair of clamping jaws 24A and 24B, a pair of actuating handles 26A and 16B, a resilient bridge section 28, and a needle holding section 30. As will be described in detail later the arms, jaws, handles and bridge section cooperate with one another to releasably mount the needle guide 20 on the ultrasound probe 10. The needle holding section 30 serves to releasably mount a needle 12 on the needle guide so that the needle extends in a desired path for introduction into the patient's body, whereupon the needle can be directed along that path to enter the patient's body and be within the field of view of the ultrasound probe, so that it can be imaged. In accordance with one preferred embodiment of this invention the needle holding section 30 is configured to provide plural discrete paths for a needle, e.g., needle 12, so that the needle can be directed as deeply as desired into the patient's body to access the desired internal structure, e.g., the femoral artery, yet be within the field of view of the ultrasound probe. As will be described later, each of those paths is established by a respective slot or channel in the needle holding section 30.

The mounting of the needle guide on the probe will also be described in detail later. Suffice it for now to state that such action is accomplished by use of the jaws 24A and 24B. In particular, those jaws are arranged to be pivoted by the arms 22A and 22B, respectively, from a normally unbiased quiescent state, like shown in FIGS. 2 and 3 wherein the jaws are spaced from each other by a minimum distance, to an open state to receive the working head 10B of the ultrasound probe. When in an open state, the jaws are separated a distance greater than the minimum distance to provide a gap therebetween which is sufficiently large to accommodate the working head 10A of the ultrasound probe in that gap irrespective of the size and shape of the working head. The opening of the jaws is accomplished by squeezing the handles 26A and 26B together. This action causes the arms to pivot outward about a pivot point (to be described later), thereby carrying the jaws 24A and 24B with them. Once the working head 10A of the ultrasonic probe is within the gap between the jaws, the handles 26A and 26B can be released, whereupon the natural bias of the resilient bridge section 28 causes the arms 22A and 22B and jaws carried by them to automatically move toward their unbiased quiescent state, whereupon the jaws will engage adjacent portions of the probe's working head to tightly clamp the working head between them. This action has the effect of releasably mounting the needle guide onto the ultrasonic probe. Once so mounted, a vascular access needle 12 can be inserted into any one of the slots or channels in the needle holding section 30 to establish the desired path for the needle to enter into the patient's body to be imaged by the ultrasonic probe.

Figure 3:
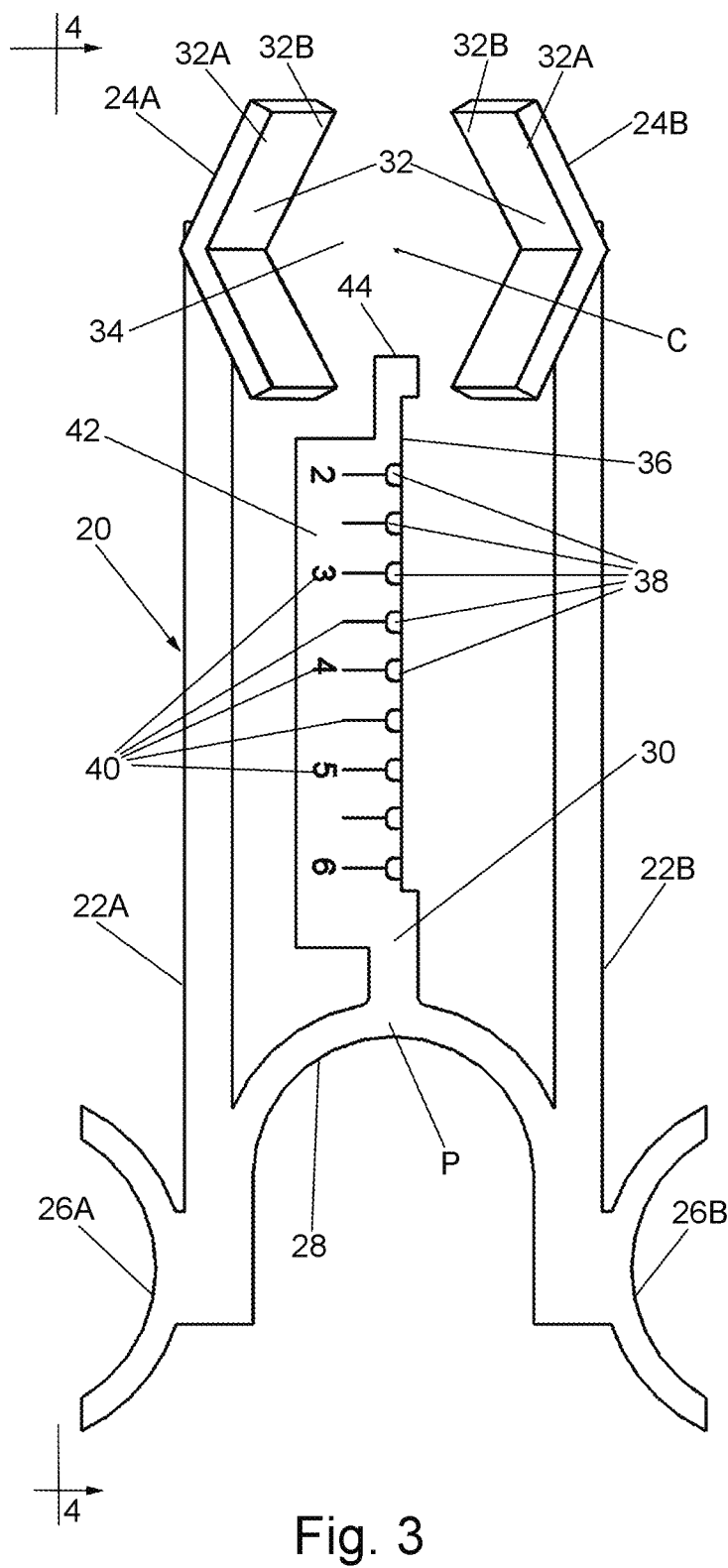
FIG. 3 is an enlarged top plan view of the needle guide of FIG. 1.

Turning now to FIG. 3, it can be seen that the pivotable arms 22A and 22B are each elongated members having a distal end and a proximal end. The jaw 24A forms the distal end of the elongated arm 22A. The jaw 24B forms the distal end of the elongated arm 22B. The actuating handle 26A forms the proximal end of the elongated arm 22A. The actuating handle 26B forms the proximal end of the elongated arm 22B. Both actuating handles 26A and 26B are in the form of concave wall sections.

The bridge section 28 is in the form of an arcuate wall connecting the proximal ends of the actuating arms 22A and 22B together at what can be considered to be a pivot point P (FIG. 3) located at the middle of the bridge section. The needle holding section 30 is in the form of an elongated extension projecting distally from the middle of the bridge section 28 and extending between the elongated arms 22A and 22B. The details of the needle holding section 30 will be described shortly.

Figure 4:
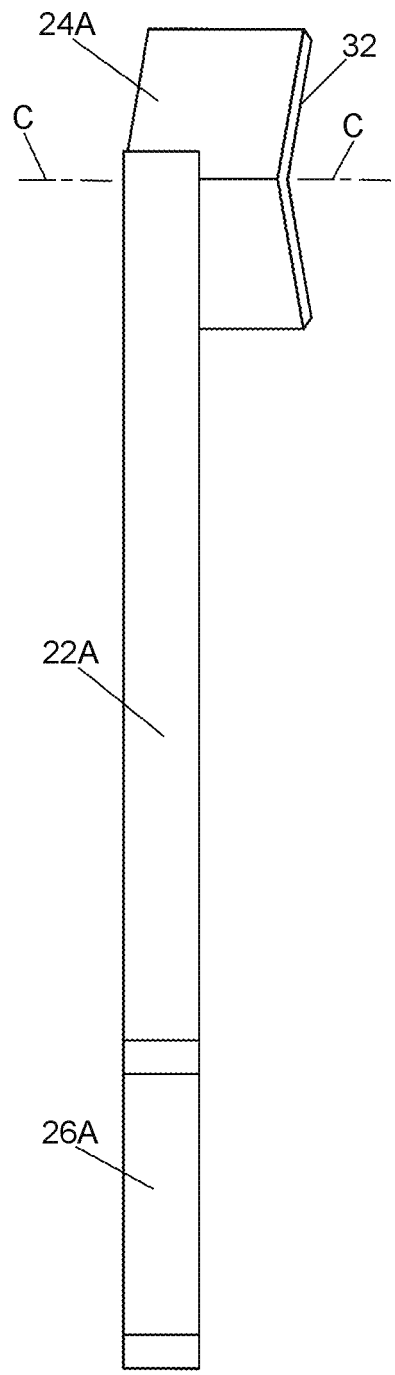
FIG. 4 is a side elevation view taken along line 4-4 of FIG. 1.

The clamping jaws 24A and 24B are of identical construction. In the exemplary embodiment shown each is in the form of a generally recessed wall-like member. In particular, each of the jaws has a generally V-shaped interior facing surface 32 having an upper portion 32A and a lower portion 32B. The interior facing surfaces of the jaws are spaced apart from each other to form the heretofore mentioned gap 34 between them. The gap 34 has a central axis C, which as can be seen in FIG. 4, is perpendicular to the plane of the pivotable arms 22A and 22B. The central axis C of the needle guide 20 will be coaxial with the central axis A of the ultrasound probe 10 when the needle guide is mounted on the working head of that probe.

As best seen in FIG. 3, the spacing between the top portions 32A of the jaws 24A and 24B of the interior facing surfaces 32 as measured from the central axis C is greater than the spacing between the bottom portions 32B of the interior facing surfaces 32 as measured from the central axis C so that the gap 34 tapers downward from the top portion 32A of the jaws to the bottom portion of the jaws. The tapering nature of the gap 34 between the jaws enables the needle guide to accommodate any type of prior art ultrasound probe (or other imaging instrument) between those jaws irrespective of the size and shape of the working head of that ultrasound probe or other imaging instrument. Thus, the needle guide device of this invention is not instrument-specific.

The details of the needle holding section 30 will now be described. As mentioned earlier the needle holding section 30 is in the form of an elongated extension that projects distally from the middle of the bridge section 28 between the elongated arms 22A and 22B. In particular, the elongated extension of making up the needle holding section is bar-like and includes a longitudinally extending planar side wall 36 (FIG. 3) having a plurality of angularly extending equidistantly spaced slots or channels 38 located therein. Each of the slots or channels 38 is linear and extends at a predetermined angle, e.g., 45 degrees, to the central axis C of the gap 34. Moreover as can be seen in FIG. 3, all of the slots or channels 38 lie in a plane that also includes the central axis C. Each slot or channel 38 is of semi-circular cross-sectional shape and of sufficient size to accommodate the gauge of any needle desired to be used with the needle guide. In one exemplary embodiment the inside diameter of each slot is approximately 0.06 inch to accommodate up to an 18 gauge needle. Other diameter slots or channels are contemplated for use with different gauge needles, depending upon the procedure to which such needles are to be put.

Each slot or channel 38 establishes a respective path or trajectory through which the needle 12 can be directed to intersect the axis C below the working head of the ultrasound probe when the needle guide is mounted thereon. Since each slot or channel will establish a different path, the needle holding section 30 includes indicia 40 to assist the user to select the desired path for the needle. In particular, the needle holding section includes indicia 40 on its top surface 42 adjacent the entryway (top) of each of the slots or channels 38. That indicia indicates the depth to which a needle extended through any particular slot or channel will intersect the axis C below the jaws. For example, the indicia 40 includes a line and an associated number "2" located on the top surface 42 of the needle holding section immediately adjacent the slot or channel 38 that is located closest to the distal end of the needle holding section. The top surface 42 immediately adjacent the next (second) proximally located slot or channel 38 has an indicia line thereat. The top surface 42 immediately adjacent the next successive (third) proximally located slot or channel 38 includes indicia 40 in the form of a line and the associated number "3" next to it. The top surface 42 adjacent the remainder of the slots or channels 38 bear similar indicia, with the most proximal slot or channel having indicia in the form of a line and the number "6" on the top surface 42 immediately adjacent that slot or channel.

The distance of each slot or channel from the axis C, coupled with the fact that the slots or channels extend at an angle, e.g., 0.45 degrees to that axis, establishes the depth at which the free end 12Bof the needle 12 will intersect that axis. Thus, for example, in the exemplary embodiment shown the slot or channel 38 disposed closest to the distal end of the needle holding section will establish a path for the needle to intersect the axis C 2 cm. below the distal end of the ultrasound probe when the needle guide is mounted on the ultrasound probe. The indicium "2" on the line next to that slot or channel indicates that fact. Thus, if the user wishes to have the needle 12 intersect the axis C 4.5 cm below the probe's working head when the needle guide 20 is mounted thereon, all the user has to do is to insert the needle into the slot or channel located between the slots or channels bearing the indicia "4" and "5".

As best seen in FIG. 1, the distal end 44 of the needle holding section 30 serves as a stop surface for engaging a portion of the working head 10B of the ultrasound probe when that working head is clamped between the jaws. Thus, the stop surface 44 assists in holding the needle guide 20 in place on the ultrasound probe 10.

Use of the needle guide device 20 will now be described. If desired a thin, flexible sheath or other cover, e.g., a latex, condom-shaped sheath (not shown) can be placed over the ultrasound probe 10 before the needle guide 20 is mounted thereon to keep the ultrasound probe sanitary. To mount the needle guide on the probe all that is required is the user to squeeze the handles 26A and 26B together about the pivot point P. This action flexes the arcuate bridge section 28 and pivots the elongated arms 22A and 22B outward with respect to each other, thereby separating or opening the jaws from their normal unbiased quiescent state and can be accomplished by the user with only one hand. Once the jaws are open, the user can place the needle guide 20 on the probe by inserting the probe's working head 10B into the tapered gap 34 between the jaws 24A and 24B and so that the stop surface 44 engages a portion of the working head. The tapering shape of the gap 34 serves to guide the insertion of the working head into proper position between those jaws. Once the working head is properly positioned between the jaws, the handles 26A and 26B can be released, whereupon the natural bias provided by the resilient bridge section 28 automatically pivots the elongated arms back together toward the unbiased quiescent state, whereupon the inner surfaces 32 of jaws will tightly sandwich the working head 10B therebetween. The needle guide is now ready to accept the needle 12. To that end, the needle is inserted into whichever slot or channel 38 is desired to carry the tip 12B of the needle into engagement with the target tissue, e.g., femoral artery. Once inserted into that particular slot or channel the needle can be pushed therealong to move the needle through that path until it is at the desired position, all the while the user can see the progress of the needle as provided by the image from the ultrasound probe. Once the needle is in its desired position, the needle guide 20 can be removed from the ultrasound probe 10, by merely squeezing its handles 26A and 26B together to separate the jaws and thus free the working head 10B from those jaws. The needle guide can be removed from the needle, leaving the needle in place by merely moving the needle guide laterally so that the needle is no longer within the slot or channel 38, whereupon the needle guide can be lifted off of the needle. The needle can then be used as desired by the user.

It should be pointed out at this juncture that the needle guide device 20 is merely exemplary of various needle guide devices that can be constructed in accordance with this invention to form a path for a needle or other elongated instrument independent of the specific imaging instrument used. Moreover, the slots or channels of the needle holding section need not be equidistantly spaced from each other or extending at the same angle to the central axis C. In fact, the angle of 45 degrees which is disclosed is only exemplary of various angles to which the slots or channels may be oriented. Further still the jaws can be shaped other than that described and shown herein so long as they form a tapering gap to facilitate the easy placement of the probe's working head therebetween.

Without further elaboration the foregoing will so fully illustrate my invention that others may, by applying current or future knowledge, adopt the same for use under various conditions of service.

The invention claimed is:

1. A needle guide configured for releasable mounting on an imaging transducer, the imaging transducer having a longitudinal central axis and working head for providing an image within a field of view of the working head, said needle guide comprising:
    a pair of elongated arms, each of said arms having a distal end portion and a proximal end portion;
    a pair of jaws, one of said pair of jaws being mounted on said distal end portion of one of said pair of elongated arms, the other of said pair of jaws being mounted on said distal end portion of the other of said pair of elongated arms, each of said jaws having an interior facing surface, said interior facing surfaces of said jaws being spaced apart from each other to form a gap therebetween, said gap having a gap central axis, each of said interior facing surfaces having a top portion and a bottom portion, with the spacing between said top portions of said interior facing surfaces as measured from said gap central axis being greater than the spacing between said bottom portions of said interior facing surfaces as measured from said gap central axis;
    a pair of handles configured to be squeezed towards each other, one of said pair of handles being connected to said proximal end portion of one of said pair of elongated arms, the other of said pair of handles being connected to said proximal end portion of the other of said pair of elongated arms;
    a bridge section connected between said pair of handles, said bridge section being resilient and configured to bend in response to the squeezing of said pair of handles towards each other to cause said distal end portions of said pair of elongated arms to pivot outward and away from each other to thereby increase the size of said gap to enable the working head of the imaging transducer to be inserted into said gap, said bridge section being configured to automatically cause said distal end portions of said pair of elongated arms to pivot inward and towards each other upon release of said handles to cause said pair of jaws to tightly sandwich the working head of the imaging transducer between said interior facing surfaces thereof; and
    a needle holding section secured to said bridge section and located between said pair of elongated arms, said needle holding section including at least one slot or channel therein extending at an angle to said gap central axis for releasably receiving a needle therein to guide said needle along a path into the field of view of the imaging transducer.

2. The needle guide of claim 1, wherein the at least one slot or channel of said needle holding section comprises plural slots or channels, each of said slots or channels being spaced from said gap central axis by a distance, with each of said distances being different, and wherein each of said slots or channels is configured for receiving a needle therein to guide the needle along a respective and different path into the field of view of the imaging transducer.

3. The needle guide of claim 2, wherein each of said plural slots or channels is oriented at a predetermined angle to said central axis.

4. The needle guide of claim 3, wherein said predetermined angle is approximately 45 degrees.

5. The needle guide of claim 2, wherein said needle holding section comprises indicia located adjacent respective ones of said plural slots or channels.

6. The needle guide of claim 1, wherein each of said interior facing surfaces of said jaws is generally V-shaped.

7. The needle guide of claim 1, wherein said handles are arcuate.

8. The needle guide of claim 1, wherein said bridge section is arcuate.

9. The needle guide of claim 1, wherein said needle guide is an integrally molded unit.

10. The needle guide of claim 1 wherein said at least one slot or channel is configured to accept a 16-18 gauge needle.

11. The needle guide of claim 2, wherein each of said interior facing surfaces of said jaws is generally V-shaped.

12. The needle guide of claim 2, wherein said handles are arcuate.

13. The needle guide of claim 2, wherein said bridge section is arcuate.

14. The needle guide of claim 2, wherein said needle guide is an integral molded member.

15. The needle guide of claim 2, wherein said at least one slot or channel is configured to accept a 16-18 gauge needle.

* * * * *